(12) United States Patent
Liu et al.

(10) Patent No.: US 11,330,767 B2
(45) Date of Patent: May 17, 2022

(54) **METHOD FOR INCREASING ARTEMISININ YIELD IN *ARTEMISIA ANNUA* L. USING BETA-OCIMENE**

(71) Applicant: HUNAN AGRICULTURAL UNIVERSITY, Changsha (CN)

(72) Inventors: Chunlin Liu, Changsha (CN); Ying Ruan, Changsha (CN); Mu Xiao, Changsha (CN); Rong Liu, Changsha (CN)

(73) Assignee: HUNAN AGRICULTURAL UNIVERSITY, Changsha (CN)

( * ) Notice: Subject to any disclaimer, the term of this patent is extended or adjusted under 35 U.S.C. 154(b) by 276 days.

(21) Appl. No.: 16/584,708

(22) Filed: Sep. 26, 2019

(65) Prior Publication Data
US 2020/0367446 A1    Nov. 26, 2020

(30) Foreign Application Priority Data
May 20, 2019   (CN) .......................... 201910418285.3

(51) Int. Cl.
*A01G 7/06*   (2006.01)
*A01H 3/04*   (2006.01)

(52) U.S. Cl.
CPC ........ *A01G 7/06* (2013.01); *A01H 3/04* (2013.01)

(58) Field of Classification Search
CPC .................................. A01G 7/06; A01H 3/04
See application file for complete search history.

(56) References Cited

FOREIGN PATENT DOCUMENTS

CN         102657042 B  *  1/2013

OTHER PUBLICATIONS

Tony R. Larson et al., "A survey of artemisinic and dihydroartemisinic acid contents in glasshouse and global field-grown populations of the artemisinin-producing plant Artemisia annua L" Industrial Crops and Products 45 (2013) 1-6. (Year: 2013).*
Graham, et al., "The Genetic Map of Artemisia annua L. Identifies Loci Affecting Yield of the Antimalarial Drug Artemisinin", Science vol. 327, 328-331 (2010).
Shen, et al., "The Genome of Artemisia annua Provides Insight into the Evolution of Asteraceae Family and Artemisinin Biosynthesis", Molecular Plant 11, 776-788, Jun. 2018.
Turconi, et al., "Semisynthetic Artemisinin, the Chemical Path to Industrial Production", 2014 American Chemical Society, Org. Process Res. Dev. 2014, 18, 417-422.
World Malaria Report 2015, World Health Organization, 280 pages.
World Malaria Report 2017, World Health Organization, 196 pages.
Xie, et al., "Artemisinin biosynthesis in Artemisia annua and metabolic engineering: questions, challenges, and perspectives", Phytochem Rev (2016) 15:1093-1114.

* cited by examiner

*Primary Examiner* — Mina Haghighatian
*Assistant Examiner* — Nathan W Schlientz
(74) *Attorney, Agent, or Firm* — Innovation Capital Law Group, LLP; Vic Lin

(57) ABSTRACT

The present invention provides a method for increasing the artemisinin yield in *Artemisia annua* L. using β-ocimene and belongs to the technical field of artemisinin production and extraction. The method treats *Artemisia annua* L. plants by β-ocimene for 1-3 d. The method selects *Artemisia annua* L. grown for at least 21 d as the object to be treated by β-ocimene. The method is very simple and can achieve multiple harvest within one year; meanwhile, it can significantly increase the artemisinin yield in *Artemisia annua* L. plant and largely increase the artemisinin yield, thereby achieving an industrialized operation.

6 Claims, 1 Drawing Sheet

METHOD FOR INCREASING ARTEMISININ YIELD IN *ARTEMISIA ANNUA* L. USING BETA-OCIMENE

CROSS-REFERENCE TO RELATED APPLICATIONS

This application claims priority to Chinese application number 201910418285.3, filed May 20, 2019, with a title of METHOD FOR INCREASING ARTEMISININ YIELD IN *ARTEMISIA ANNUA* USING β-OCIMENE. The above-mentioned patent application is incorporated herein by reference in its entirety.

TECHNICAL FIELD

The present invention belongs to the technical field of artemisinin production and extraction, and particularly relates to a method for increasing the artemisinin yield in *Artemisia annua* L. using β-ocimene.

BACKGROUND

Artemisinin is a sesquiterpene lactone drug having a peroxide group which is extracted from *Artemisia annua* L., and is the best drug for treating malaria. The Artemisinin-Based Combination Therapy (ACT) has become the first line therapy for *falciparum* infection in more than 80 endemic countries since World Health Organization (WHO) recommended artemisinin for treating malaria in 2002 (WHO (2015) Changes in malaria incidence and mortality. In: WHO Global Malaria programme-World Malaria Report 2015: World Health Organization; WHO (2017) Changes in malaria incidence and mortality. In: WHO Global Malaria programme-World Malaria Report 2017: World Health Organization). Since artemisinin was discovered in 1970s, it has saved more than 1 billion people in areas at high risk of malaria (WHO) 2017 Changes in malaria incidence and mortality. In: WHO Global Malaria programme-World Malaria Report 2017: World Health Organization). However, global artemisinin yield still cannot completely meet the demands of preventing and treating malaria due to two main reasons: one is that the artemisinin yield in *Artemisia annua* is low, which is about 0-0.8% dry weight (Xie, D.-Y., Ma, D.-M., Judd, R., and Jones, A. L. (2016). Artemisinin biosynthesis in *Artemisia annua* L. and metabolic engineering: questions, challenges, and perspectives. Phytochemistry Rev 15:1093-1114); the other is that *Artemisia annua* is a field crop which is harvested once in one year, and is easily affected by weather factors and plant diseases and pests etc., so the final yield fluctuating greatly. Just because of the limited source and unstable production of artemisinin, the artemisinin yield in each year cannot completely meet the demands of Artemisinin-Based Combination Therapy. The gap between the demands and production has become one of the main and direct reasons causing the deaths of about 450 thousand people in each year. Since malaria areas mainly is economically underdeveloped areas, such as southeast Asia and Africa, the United Nations needs to purchases plenty of artemisinin with low cost and price for these areas each year. However, the actual demand cannot be satisfied completely. To solve this problem, in the last few decades, people has put a lot of effort, such as breeding varieties having high artemisinin yield by breeding means (Graham I A, Besser K, Blumer S, Branigan C A, Czechowski T, Elias L, Guterman I, Harvey D, Isaac P G, Khan A M. (2010) The genetic map of *Artemisia annua* L. identifies loci affecting yield of the antimalarial drug artemisinin. Science 327:328-331); using tobacco or yeasts for producing artemisinin or the derivatives thereof by metabolic engineering methods (Turconi, J., Griolet, F., Guevel, R., Oddon, G., Villa, R., Geatti, A., Hvala, M., Rossen, K., Goller, R., and Burgard, A. (2014). Semisynthetic artemisinin, the chemical path to industrial production. Org Process Res Dev, 18:417-422; Shen Q., Zhang L., Liao Z., Wang S., Yan T., Shi P., Liu M., Fu X., Pan Q., Wang Y., Lv Z., Lu X., Zhang F., Jiang W., Ma Y., Chen M., Hao X., Li L., Tang Y., Lv G., Zhou Y., Sun X., Brodelius P. E., Rose J. K. C., and Tang K. (2018). The Genome of *Artemisia annua* Provides Insight into the Evolution of Asteraceae Family and Artemisinin Biosynthesis. Mol. Plant. 11, 776-788); In the end of 2017, Bill and Melinda Gates Foundation supported again a chemical method for converting a precursor substance into artemisinin at a scale of 50 ton. However, these different methods increasing artemisinin yield or yield have each technical limitations, until now, the shortage of low price artemisinin still has not been solved.

SUMMARY

In view of this, an objective of the present invention is to provide a method for increasing the artemisinin yield in *Artemisia annua* L. using β-ocimene. The method has a simple operation and short production cycle, and can significantly increase the artemisinin yield in *Artemisia annua* L.

In order to achieve the foregoing invention objective, the present invention provides the following technical solution.

A method for increasing the artemisinin yield in *Artemisia annua* L. using β-ocimene includes treating *Artemisia annua* L. plants by β-ocimene for 1-3 d.

Preferably, the *Artemisia annua* L. plants are *Artemisia annua* L. plants which have grown at least 21 d since being sowed.

Preferably, the *Artemisia annua* L. plants are *Artemisia annua* L. plants which have grown 21 d since being sowed.

Preferably, the treatment is placing the *Artemisia annua* L. plants in an enclosed space containing volatilized β-ocimene.

Preferably, the β-ocimene in the enclosed space has a concentration of 1-30 μmol/L.

Preferably, the β-ocimene in the enclosed space has a concentration of 5-20 μmol/L.

Preferably, the β-ocimene volatilization is achieved by adding dropwise β-ocimene onto a glass slide which has been preheated to 35-45° C.

Preferably, the time of treating *Artemisia annua* L. plants by β-ocimene is 1.5-2.5 d.

The beneficial effects of the present invention are: the method for increasing the artemisinin yield in *Artemisia annua* L. using β-ocimene provided by the present invention treats *Artemisia annua* L. plant by β-ocimene for 1-3 d; the method is very simple and can achieve an industrialized operation, meanwhile, it can significantly increase the artemisinin yield in *Artemisia annua* L. plant. The artemisinin yield in *Artemisia annua* L. plant can achieve 2.5% dry weight, and in the conventional method of using *Artemisia annua* L. for producing artemisinin, the average yield of artemisinin in *Artemisia annua* L. plant in the field is about 0.8% dry weight. So the artemisinin yield in the method of the present invention is increased more than 3 times. The method of the present invention can largely increases the artemisinin yield.

Furthermore, in the conventional method, *Artemisia annua* L. plants grow for more than 6 months, then the raw material is harvested for extracting artemisinin; however, in the method of the present invention, *Artemisia annua* L. plants which have grown 18-24 d are treated for 1-3 d, and the artemisinin yield in *Artemisia annua* L. can be significantly increased. The *Artemisia annua* L. plants are harvested for artemisinin extraction. The entire production cycle of artemisinin is significantly shortened to 19-27 d; and *Artemisia annua* L. containing high artemisinin can be harvested many times in one year.

DETAILED DESCRIPTION

Figure 1:
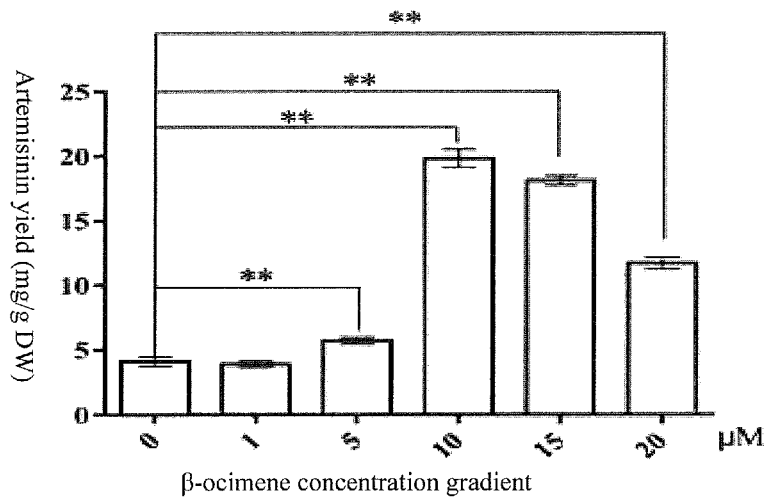
FIG. 1 is the artemisinin yield in *Artemisia annua* L. plants treated by different concentrations of β-ocimene with the same treatment times.

The present invention provides a method for increasing the artemisinin yield in *Artemisia annua* L. using β-ocimene, which treats *Artemisia annua* L. plant by β-ocimene for 1-3 d.

In the present invention, the *Artemisia annua* L. plants are *Artemisia annua* L. plants which have grown at least 21 d since being sowed; more preferably, the *Artemisia annua* L. plants are *Artemisia annua* L. plants which have grown 21 d since being sowed. In the present invention, the age of *Artemisia annua* L. plants is considered synthetically by many factors, such as the size of the enclosed space, the yield and the harvest cycle. In the present invention, *Artemisia annua* L. plants which have grown 21 d are preferably selected, the growth time is short, and is conducive to harvesting many times within one year. In the present invention, preferably, *Artemisia annua* L. seeds are sterilized and then are sowed and grown, and the *Artemisia annua* L. plants are obtained. In the present invention, preferably, the sanitizer is 70% aqueous ethanol (V/V); preferably, the sterilization time is 8-12 min and more preferably 10 min. In the present invention, after the sterilization, preferably, the sterilized seeds are washed by clear water. Preferably, the seeds are washed 3-5 times, and more preferably 4 times. In the present invention, preferably, the sterilized *Artemisia annua* L. seeds are sowed into pods containing nutrient soil. In the present invention, preferably, the growth temperature is 24-26° C., and more preferably 25° C. Preferably, the illumination time of the growth is 16 h light/8 h dark; the illumination is provided by T5 efficient energy-saving fluorescent lamp of Sanxiong Aurora Lighting Technology Co., Ltd. Preferably, the illumination intensity is 180 μmol light quantum $m^{-2} s^{-1}$.

In the present invention, *Artemisia annua* L. plants are treated by β-ocimene, preferably, the treatment is placing the *Artemisia annua* L. plants in an enclosed space containing volatilized β-ocimene. In the present invention, preferably, the β-ocimene in the enclosed space has a concentration of 1-30 μmol/L, and more preferably 5-20 μmol/L, and most preferably 10 μmol/L. The present invention has no special requirements on the size and type of the enclosed space but that the space is enclosed. The enclosed space includes but is not limited to small enclosed containers and a greenhouse. When the enclosed space is a greenhouse, preferably, the *Artemisia annua* L. plants are *Artemisia annua* L. plants which have grown 35 d since being sowed. In the specific implementation of the present invention, preferably, the enclosed space is provided by a transparent and enclosed dryer; preferably, the dryer volume is 8-12 L, more preferably 10 L. In the present invention, the β-ocimene volatilization is achieved by adding dropwise β-ocimene onto a glass slide which has been preheated to 35-45° C., more preferably, has been preheated to 40° C. In the present invention, one *Artemisia annua* L. plant is transferred into one dryer; preferably, the *Artemisia annua* L. plant growing in a pod is transferred with the pod. In specific implementation of the present invention, *Artemisia annua* L. plants are transferred, at the same time, the preheated glass slide is placed into the dryer, and β-ocimene is added dropwise onto the glass slide; in the present invention, when above operations are completed, preferably, the dryer is enclosed rapidly.

In the present invention, the time of treating *Artemisia annua* L. plants by β-ocimene is 1-3 d, preferably 1.5-2.5 d. In the present invention, after being treated by β-ocimene, preferably, the *Artemisia annua* L. plants are transferred out from the dryer. The overground parts of the *Artemisia annua* L. plants are taken, then are dried for 2 d under 45° C., and ground to powder for artemisinin extraction.

The technical solution provided by the present invention will be described in detail in connection with the following embodiments, but they should not be construed as a limitation to the claimed scope of the present invention.

Embodiment 1

β-ocimene is purchased from Sigma-Aldrich, the number is W353901.

*Artemisia annua* L. seeds are subjected to a surface sterilization by 70% ethanol (V/V) of 10 min, then are washed by clear water for 4 times. The sterilized seeds are sowed into pods containing nutrient soil, then is growing in a greenhouse of 16 h light/8 h dark at the temperature of 25±1° C. for 3 weeks. The *Artemisia annua* L. plants which have grown 3 weeks are transferred into 10 L transparent and enclosable dryers with the pods, 1 plant is transferred into each container. At the same time, one glass slide which has been preheated at 40° C. is placed into the dryer, volatile analytically pure β-ocimene is added dropwise onto the glass slide; then the dryer is enclosed rapidly. The *Artemisia annua* L. plants in enclosed containers without β-ocimene are used as the control.

After β-ocimene volatilizes, the final β-ocimene concentrations in the air of the container are 0, 1, 5, 10, 15 and 20 μmol/L respectively, and the treatment time of each concentration is 24 h. Then, the *Artemisia annua* L. plants are transferred out the enclosed containers. The overground parts of the *Artemisia annua* plants are taken, then is dried for 2 d under 45° C., ground to powder for the next step, artemisinin extraction.

0.1 g dried powder is taken and poured into a centrifuge tube, 2 mL methanol is added therein and mixed homogeneously, and then subjected to an ultrasound treatment by an ultrasonic apparatus for 30 min. After centrifuged for 10 min at 1669×g, the supernatant is transferred into a 5 mL centrifuge tube, then the residue is extracted by methanol again. The second supernatant is mixed with first one. The mixture is filtered by a 0.22 μm aperture diameter filter, the filtrate is used for the determination of artemisinin yield; and the filtrate is dried, so artemisinin product is obtained.

Determination of Artemisinin Yield

HPLC-DAD separation detection system is Agilent Infinity 1260 (Diomosil C18 column of DiKMA, 5 μm, 250 mm, 4.5 mm); where the mobile phase is methanol/water 6:4; the flow rate is 1 mL/min. The sample size is 10 μL, the retention time is 8.3±0.03 min; and the absorption peak is 230 nm. Standard artemisinin sample (purchased from Sigma-Aldrich) is used for drawing the standard curve, the concentration gradient is 0.3125, 0.625, 1.25, 2.5 and 5 μg/10 μL. According to the absorbance detection results of different standard sample concentrations, linear regression equation $Y=0.0056X-3.0408$ is obtained, where the correlation coefficient is $R^2=0.9909$ for calculation; in the equation, X is peak area, and Y is the artemisinin yield in each 10 μL detection sample (μg). Same parameters are used for the determination of the artemisinin absorbance in each sample, and the artemisinin yield in each sample is calculated by above linear regression equation. The results are shown by FIG. 1 and table 1. As the β-ocimene concentration rises, the artemisinin yield in plants which have been treated for 24 h first rises, and then decreases, and when the β-ocimene concentration achieves 10 μmol/L, the artemisinin yield in plants reaches the highest level.

TABLE 1 artemisinin yield in plants treated by different concentrations of β-ocimene

| β-ocimene concentration (μmol/L) | Artemisinin yield (mg/g DW) | | |
|---|---|---|---|
| Concentration gradients | 1 | 2 | 3 |
| 0  | 4.1  | 4.5  | 3.8  |
| 1  | 3.8  | 3.8  | 4.2  |
| 5  | 5.5  | 6.1  | 5.7  |
| 10 | 19.9 | 19.1 | 20.5 |
| 15 | 18   | 17.8 | 18.5 |
| 20 | 11.7 | 12.2 | 11.3 |

Embodiment 2

β-ocimene is purchased from Sigma-Aldrich, the number is W353901.

*Artemisia annua* L. seeds are subjected to a surface sterilization by 70% ethanol (V/V) of 10 min, then are washed by clear water for 4 times. The sterilized seeds are sowed into pods containing nutrient soil, then is growing in a greenhouse of 16 h light/8 h dark at the temperature of 25±1° C. for 3 weeks. The *Artemisia annua* plants which have grown 3 weeks are transferred into 10 L transparent and enclosable dryers with the pods, 1 plant is transferred into each container. At the same time, one glass slide which has been preheated at 40° C. is placed into the dryer, volatile analytically pure β-ocimene is added dropwise onto the glass slide; then the dryer is enclosed rapidly. The *Artemisia annua* L. plants in enclosed containers without β-ocimene are used as the control.

After β-ocimene volatilizes, the final β-ocimene concentration in the air of the container is 10 μmol/L, and the treatment time was set for 6, 12, 24, 48, 72 and 96 h. Then, the *Artemisia annua* L. plants are transferred out the enclosed containers. The overground parts of the *Artemisia annua* L. plants are taken, then is dried for 2 d under 45° C., ground to powder for the next step, artemisinin extraction.

0.1 g dried powder is taken and poured into a centrifuge tube, 2 mL methanol is added therein and mixed homogeneously, and then subjected to an ultrasound treatment by an ultrasonic apparatus for 30 min. After centrifuging for 10 min at 1669×g, the supernatant is transferred into a 5 mL centrifuge tube, then the residue is extracted by methanol again. The second supernatant is mixed with the first one. The mixture is filtered by a 0.22 μm aperture diameter filter, the filtrate is used for the determination of artemisinin yield; and the filtrate is dried, so artemisinin product is obtained.

Determination of Artemisinin Yield

HPLC-DAD separation detection system is Agilent Infinity 1260 (Diomosil C18 column of DiKMA, 5 μm, 250 mm, 4.5 mm); where the mobile phase is methanol/water 6:4; the flow rate is 1 mL/min. The sample size is 10 μL, the retention time is 8.3±0.03 min; and the absorption peak is 230 nm. Standard artemisinin sample (purchased from Sigma-Aldrich) is used for drawing the standard curve, the concentration gradient is 0.3125, 0.625, 1.25, 2.5 and 5 μg/10 μL. According to the absorbance detection results of different standard sample concentrations, linear regression equation $Y=0.0056X-3.0408$ is obtained, where the correlation coefficient is $R^2=0.9909$ for calculation; in the equation, X is peak area, and Y is the artemisinin yield in each detection sample treated by 10 μmol/L β-ocimene. Same parameters are used for the determination of the artemisinin absorbance in each sample, and the artemisinin yield in each sample is calculated by above linear regression equation.

Figure 2:
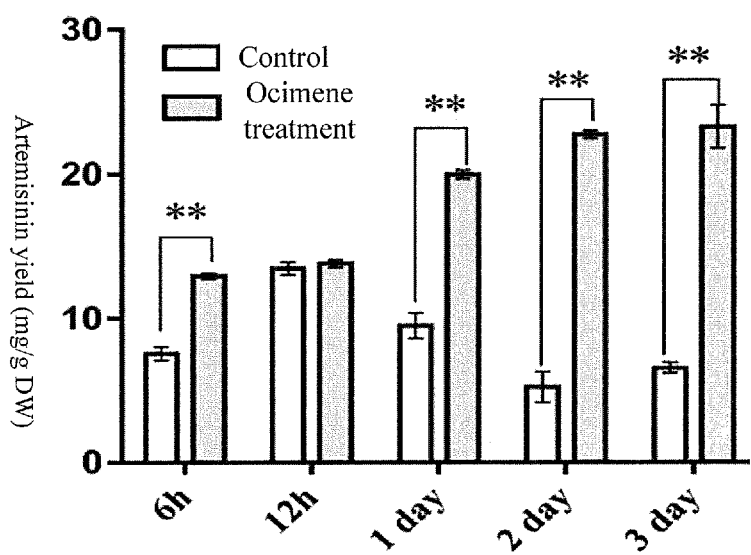
FIG. 2 is the artemisinin yield in *Artemisia annua* L. plants treated by the same concentration of β-ocimene with different treatment times.

The different treatment times of β-ocimene are 0, 6, 12, 24, 48 and 72 h. The results are shown by FIG. 2 and table 2. Following treatment with 10 μmol/L β-ocimene for 6, 12, 24, 48 and 72 h, the artemisinin yield in treated plants continuously rise, and is significantly increased compared with the control.

TABLE 2

Artemisinin yield in plants treated by different times of β-ocimene

| Treatment time | Control group (mg/g DW) | | | Experiment group (mg/g DW) | | |
|---|---|---|---|---|---|---|
| Replications | 1 | 2 | 3 | 1 | 2 | 3 |
| 6 h  | 7.3  | 7.3  | 8.1 | 13   | 13.1 | 12.7 |
| 12 h | 13.9 | 13.5 | 13  | 14   | 14   | 13.5 |
| 1 d  | 10.2 | 9.8  | 8.5 | 20   | 19.7 | 20.3 |
| 2 d  | 4.1  | 5.4  | 6.2 | 23.1 | 22.5 | 22.7 |
| 3 d  | 6.2  | 6.6  | 6.9 | 22.3 | 25   | 22.5 |

It can be known from the foregoing embodiments that the method provided by the present invention has a simple operation and shortened production cycle, and can significantly increase the artemisinin yield in *Artemisia annua* L., so it is applicable to industrial production.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for increasing the artemisinin yield in *Artemisia annua* L. using β-ocimene, comprising treating *Artemisia annua* L. plants with β-ocimene for 1-3 d, wherein the *Artemisia annua* L. plants are *Artemisia annua* L. plants which have grown 21 d since being sowed.

2. The method according to claim 1, wherein the treatment is placing the *Artemisia annua* L. plants in an enclosed space containing volatilized β-ocimene.

3. The method according to claim 2, wherein the β-ocimene in the enclosed space has a concentration of 1-30 μmol/L.

4. The method according to claim 3, wherein the β-ocimene in the enclosed space has a concentration of 5-20 μmol/L.

5. The method according to claim 2, wherein the β-ocimene volatilization is achieved by adding dropwise β-ocimene onto a glass slide which has been preheated to 35-45° C.

6. The method according to claim 1, wherein the *Artemisia annua* L. plants are treated with β-ocimene for 1.5-2.5 d.

* * * * *